United States Patent
Bradley

(10) Patent No.: US 7,103,403 B1
(45) Date of Patent: *Sep. 5, 2006

(54) IMPLANTABLE CARDIAC STIMULATION SYSTEM AND METHOD FOR MONITORING DIASTOLIC FUNCTION

(75) Inventor: Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 10/894,800

(22) Filed: Jul. 19, 2004

Related U.S. Application Data

(63) Continuation of application No. 09/996,306, filed on Nov. 21, 2001, now Pat. No. 6,810,284.

(51) Int. Cl.
*A61N 1/37* (2006.01)
(52) U.S. Cl. .......................... 600/510; 607/27
(58) Field of Classification Search ........ 600/508–510; 607/9, 17, 24–28
See application file for complete search history.

(56) References Cited

U.S. PATENT DOCUMENTS

| | | | |
|---|---|---|---|
| 5,334,222 A | 8/1994 | Salo et al. ................. | 607/17 |
| 5,476,483 A | 12/1995 | Bornzin et al. ............. | 607/17 |
| 5,534,016 A * | 7/1996 | Boute ........................ | 607/9 |
| 5,643,327 A | 7/1997 | Dawson et al. ............. | 607/24 |
| 6,389,316 B1 * | 5/2002 | Bornzin et al. ............. | 607/28 |
| 6,473,647 B1 * | 10/2002 | Bradley ..................... | 607/27 |
| 6,810,284 B1 * | 10/2004 | Bradley ..................... | 600/510 |

OTHER PUBLICATIONS

Belz, Michael K., et al., The Effect of Left Ventricular Intracavitary Volume on the Unipolar Electrogram, PACE, vol. 16, Sep. 1993, pp. 1842-1852.

Aronow, W.S., et al., Prognosis of Congestive Heart Failure in Elderly Patients with Normal Versus Abnormal Left Ventricular Systolic Function Associated with Coronary Artery Disease, American Journal of Cardiology, pp. 1257-1259, vol. 66 (Nov. 15, 1990).

* cited by examiner

*Primary Examiner*—Robert E. Pezzuto
*Assistant Examiner*—Kristen Mullen

(57) ABSTRACT

A cardiac stimulation device and method perform a diastolic function test during which an amplitude-based feature of an evoked response is determined for a number of AV or PV delay settings. Stimulation operating parameters may be adjusted in response to a detected change in diastolic function. The diastolic function test may be repeated periodically with results stored in memory for later downloading to an external device allowing a physician to monitor the diastolic response to a selected treatment.

22 Claims, 7 Drawing Sheets

IMPLANTABLE CARDIAC STIMULATION SYSTEM AND METHOD FOR MONITORING DIASTOLIC FUNCTION

CROSS-REFERENCE TO RELATED APPLICATIONS

This application is a continuation of U.S. patent application Ser. No. 09/996,306, filed Nov. 21, 2001, now U.S. Pat. No. 6,810,284 B1.

FIELD OF THE INVENTION

The present invention relates generally to an implantable cardiac stimulation device. More specifically, the present invention is directed to a method for monitoring cardiac function using an implantable cardiac stimulation device.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. One or more heart chambers may be electrically stimulated depending on the location and severity of the conduction disorder.

A single-chamber pacemaker delivers pacing pulses to one chamber of the heart, either one atrium or one ventricle. Dual chamber pacemakers are now commonly available and can provide stimulation in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g., the right atrium), and a separate unipolar or bipolar lead extends from a ventricular channel to the corresponding ventricle (e.g., the right ventricle). In dual chamber, demand-type pacemakers commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (a P-wave) is not detected by the atrial channel, a stimulating pulse will be delivered to depolarize the atrium and cause contraction. Following either a detected P-wave or an atrial stimulation pulse, the ventricular channel attempts to detect a depolarization signal in the ventricle, known as an R-wave. If no R-wave is detected within a defined interval, a stimulation pulse is delivered to the ventricle to cause ventricular contraction. In this way, rhythmic dual chamber pacing is achieved by coordinating the delivery of ventricular output in response to a sensed or paced atrial event.

The interval following an atrial stimulation pulse prior to delivery of a ventricular stimulation pulse is commonly referred to as an "AV delay." The interval following an atrial sensed P-wave prior to delivering a ventricular stimulation pulse is commonly referred to as a "PV delay." The AV delay is typically programmed to be longer than a PV delay because an atrial stimulation pulse is delivered at a location away from the direct conduction path of an intrinsic depolarization arising from the sinus node and traveling to the ventricles.

It is known that the AV and PV delay settings during dual chamber pacing can have profound effects on hemodynamic function, particularly in patients suffering from heart failure. Extreme differences in cardiac output can result from different AV and PV delay settings. Mounting clinical evidence supports the use of dual chamber or multi-chamber stimulation in patients suffering from congestive heart failure even if normal conduction pathways are intact. In these patients, the therapeutic benefit of cardiac stimulation is thought to be derived from a resynchronization of the heart chamber contractions. The dilatation of the heart that occurs with the progression of heart failure impairs the normal synchrony of heart chamber contractions. Therefore, careful selection of the AV and PV delays in these patients can provide hemodynamic benefit.

Methods used by physicians to monitor the progression of heart failure or a response to heart failure therapy include echocardiographic techniques for measuring heart dimensions and estimating ejection fraction, catheterization techniques for measuring blood pressures and volumes, and exercise testing. These monitoring methods can only be performed periodically in a clinical setting and can be costly as well as pose additional risk to the patient.

Numerous attempts have been made, therefore, to develop an implantable cardiac stimulation device that includes one or more physiological sensors for measuring cardiac function. Proposed methods have suggested using pressure sensors, flow transducers, impedance measurement for estimating chamber volumes, accelerometers for detecting heart motion, temperature sensors, pH sensors, and oxygen sensors for monitoring heart function. The difficulty in incorporating such sensors in an implantable cardiac stimulation device is the added hardware and complex circuitry needed to support and process sensor data. For example, both the blood ejection phase of the cardiac cycle, known as "systole", and the filling phase of the cardiac cycle, known as "diastole", can be impaired in congestive heart failure. In fact, congestive heart failure symptoms may be attributed to diastolic dysfunction in a significant number of congestive heart failure patients. Diastolic dysfunction is particularly common in elderly patients.

Clinically, diastolic dysfunction is difficult to detect and assess without performing echocardiography. Diastolic dysfunction may be present when systolic function is adequate and symptoms of congestive heart failure are absent. Treatments for diastolic dysfunction therefore remain relatively under-investigated. Monitoring of diastolic function over time, using a method that does not require expensive or invasive methods that can be performed in a clinic would be advantageous in diagnosing diastolic dysfunction and optimizing its treatment.

The cardiac signal produced in response to a stimulation pulse that depolarizes the heart has been found to be proportional to ventricular chamber volume. When a stimulation pulse is delivered to a ventricle, an evoked response electrocardiogram signal is produced. The integral of the negative portion of the evoked response signal, referred to hereafter as the "paced depolarization integral," has been found to be inversely proportional to end-diastolic volume. The paced depolarization integral has already been proposed as a measure of cardiac volume upon which adjustments in AV delay can be based in an effort to maximize the heart's ejected blood volume during cardiac stimulation.

It would be desirable, however, to also provide a diagnostic method for monitoring changes in heart function over time using an implantable cardiac stimulation device without requiring additional physiological or metabolic sensors. In particular, it would be desirable to monitor diastolic function over time using the paced depolarization integral so that worsening or improving diastolic function can be tracked and therapy delivery could be adjusted accordingly. Preferably, this is accomplished using standard sensing of internal cardiac electrogram (EGM) signals without complex software requirements and without requiring physician office visits.

SUMMARY OF THE INVENTION

The present invention addresses this need by providing an implantable cardiac stimulation device and associated method for monitoring diastolic function based upon the measurement of the cardiac evoked response and calculation of one or more amplitude-based features, such as the peak negative amplitude or the paced depolarization integrals of the evoked response. The filling time of the ventricles is increased as the length of the cardiac cycle increases or as the AV and PV delays are increased. With increased filling time, ventricular end-diastolic volume will increase. The amplitude-based features of the ventricular evoked response decrease with increasing end-diastolic volume (inversely proportional). Thus, as the AV or PV delay or the cycle lengths are increased, the amplitude-based features will decrease. This relation can be represented as a slope of the amplitude-based feature plotted versus AV or PV delay or cycle length.

In patients having diastolic dysfunction, the increase in end-diastolic volume with increased filling time is less than in normal patients. Therefore, if the amplitude-based features of the evoked response decrease to a lesser degree than normal with increased filling time, resulting in a less negative slope, diastolic function has worsened. If the amplitude-based features decrease to a greater degree with increased filling time, resulting in a more negative slope, then diastolic function has improved.

Thus, one embodiment is a cardiac stimulation device and method for determining the slope of an amplitude-based feature of the evoked response and filling time relationship, for the purposes of assessing diastolic function.

In another embodiment, a method is provided in which changes in diastolic function can be determined over time so that diastolic dysfunction may be diagnosed and tracked by a physician, who may then make treatment decisions based on such information.

According to one embodiment, a control system of the implanted stimulation device executes a diastolic function test by delivering ventricular stimulation pulses at varying delays following an atrial stimulation pulse (AV delay) or an atrial sensed P-wave (PV delay), and then monitoring one or more amplitude-based features of the evoked responses.

In an alternative embodiment, the ventricular escape interval can be varied during the diastolic function test rather than AV and PV delay.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing automatic monitoring of diastolic function in a cardiac stimulation device. A general cardiac stimulation device will be described in conjunction with FIGS. 1 and 2, in which an automatic diastolic function test, as provided by the present invention, could be implemented. It is recognized, however, that numerous variations of such a device exist in which the methods to be described herein could be implemented without deviating from the scope of the present invention.

Figure 1:
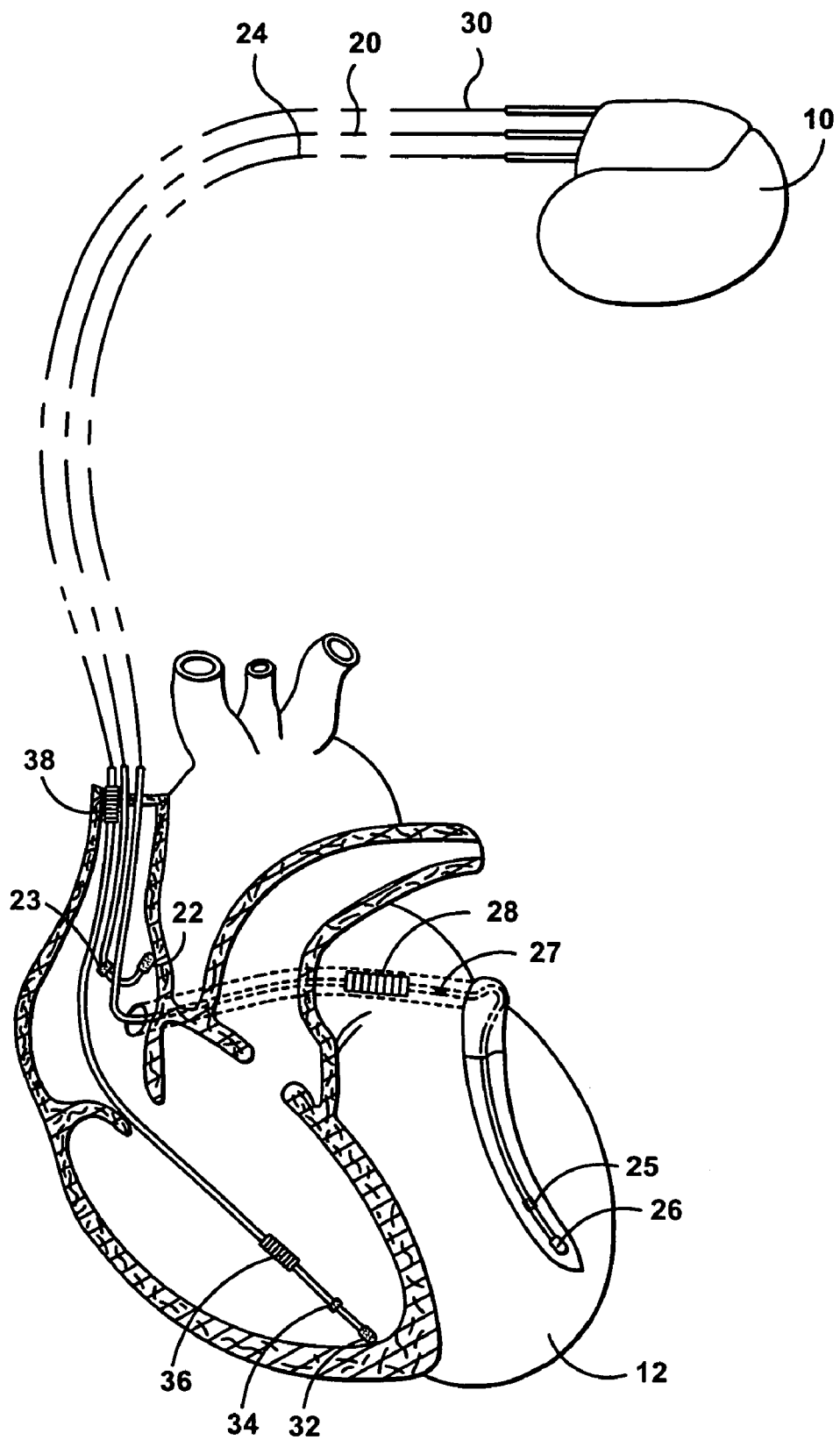
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place at least a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to: deliver left ventricular stimulation therapy using at least a left ventricular tip electrode 26 for unipolar configurations or in combination with left ventricular ring electrode 25 for bipolar configurations; left atrial stimulation therapy using at least a left atrial ring electrode 27, and shocking therapy using at least a left atrial coil electrode 28. The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
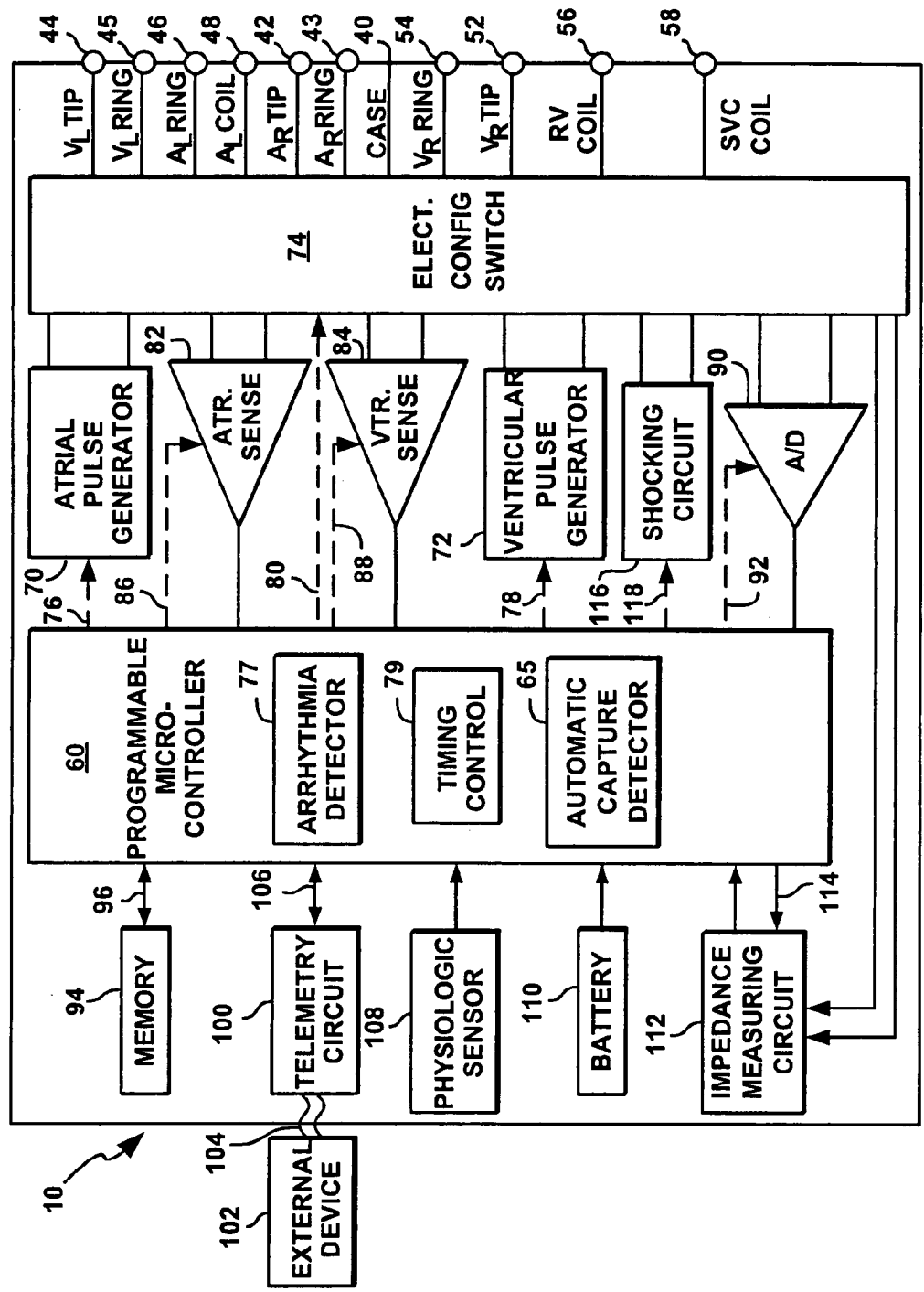
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for "unipolar" modes. The housing 40 may further be used as a return electrode alone or in combination with one or more of the coil electrodes 28, 36, or 38, for defibrillation shocking purposes. The stimulation device 10 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrial-ventricular (AV) delay, atrial interconduction (A—A) delay, or ventricular interconduction (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate ventricular tachycardia, high rate ventricular tachycardia, and fibrillation rate zones) and various other characteristics (e.g., sudden onset, stability, physiologic sensors, and morphology, etc.), in order to determine the type of remedial therapy that is needed (e.g., bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract.

In the embodiment shown in FIG. 2, the microcontroller 60 includes an automatic capture detector 65 that searches for a depolarization signal, known as an evoked response signal, following a stimulation pulse during a "detection window" set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

Preferably, designated blocks of memory cells located in memory 94 may be used to store cardiac data. In accordance with the present invention, a block of memory cells is designated to store diastolic function data. Diastolic function data that has been collected by microprocessor 60 and stored in memory 94 may be downloaded to the external device 102 via telemetry circuit 100.

The stimulation device 10 further includes a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting resting and active states). Accordingly, the microcontroller 60 responds by adjusting various stimulation parameters (such as rate, AV Delay, V—V Delay, etc.) at which the atrial and ventricular pulse generators 70 and 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. A posture sensor may be used for detecting when a patient is lying down, which can be used in combination with an activity or other metabolic sensor for determining if a patient is at rest. The diastolic function test included in the present invention is preferably performed once a patient has reached a predetermined resting state. Therefore, any sensor may be used in the present invention which is capable of sensing a physiological parameter that corresponds to the activity level of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 µA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112, which is enabled by the microcontroller 60 by a control signal 114. The known uses for an impedance measuring circuit 112 include, for example, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
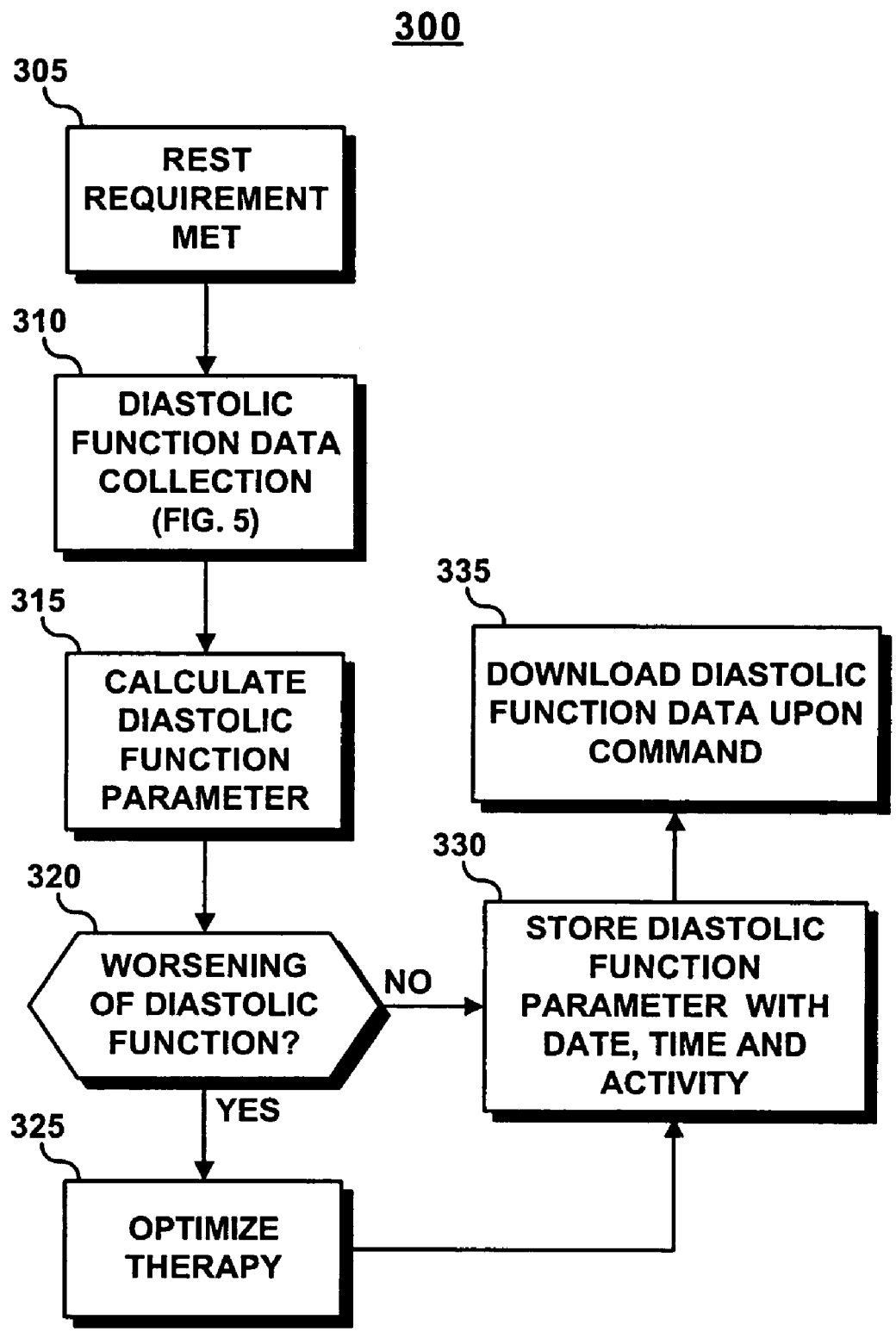
FIG. 3 is a flow chart illustrating a process for performing a diastolic function test in the device of FIG. 2, according to the present invention.

In FIG. 3, a flow chart is shown describing an overview of the operation and novel features implemented in one embodiment of the device 10 for monitoring diastolic function. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

In the embodiment shown in FIG. 3, the diastolic function test is preferably performed while the patient is at rest. Therefore at step 305, microprocessor 60 begins by determining if a required resting state is met. A resting state of the patient is indicated by physiological sensor 108 which may be an activity sensor, a minute volume sensor or any other sensor or combination of sensors capable of providing a signal for detecting a resting state of the patient. The device 10 may also define a rest state as the pacemaker pacing base rate (such as a fixed base rate) for a predetermined programmable period of time.

The rest requirement may further require that the patient be at rest for a minimum period of time, for example several minutes, prior to initiating the diastolic function test. Physiological sensor 108 may include a posture sensor so that the diastolic function test may also be performed when the patient is determined to be supine. Differences in diastolic function may exist due to gravitational effects when the patient is standing versus lying down.

An activity variance signal could be used to detect extended periods of rest, normally at night, as opposed to daytime activity, in order to perform the diastolic function test under both conditions. Thus, based on an activity sensor, a posture sensor, or an activity variance signal or a combination of these, the physician is able to program the device 10 to perform a diastolic function test preferentially during resting or waking hours, or while the patient is standing or supine.

The diastolic function may be performed one time after a user-programmed command has enabled it and the desired resting state has been reached at step 305. Alternatively, the diastolic function test may be programmed to be repeated after a specified time interval, for example daily or weekly, during periods of rest that meet the requirement at step 305.

After the desired rest (or posture) state of the patient is reached at step 305, data pertaining to the diastolic function of the patient is collected at step 310 and stored in memory 94. An exemplary embodiment of methods used to collect the diastolic function data will be described with reference to FIGS. 5 through 7. In the following description of an exemplary preferred embodiment, the paced depolarization integral will be considered as the preferred amplitude-based parameter of the evoked response used for the diastolic function parameter. It should however be understood that any suitable amplitude-based parameters of the evoked response may be used.

Briefly, during the data collection, paced depolarization integrals will be obtained for a number of AV or PV delay settings or escape interval settings. As will be described, an average paced depolarization integral is calculated for each delay or escape interval setting.

After the data collection step 310 is completed, a diastolic function parameter is calculated at step 315. The diastolic function parameter is the slope of the relationship between the delay or escape interval settings and the average paced depolarization integrals. Ventricular filling time varies directly with variations in the AV or PV delay or escape interval settings, and as filling time increases, end-diastolic volume will increase. The paced depolarization integral is inversely proportional to end-diastolic volume. Therefore, the slope of the relationship between filling time (represented by the AV or PV delay or escape interval) and the paced depolarization integral data is negative and becomes more negative as diastolic function improves and less negative as diastolic function worsens. This relationship is further illustrated in FIG. 4.

Figure 4:
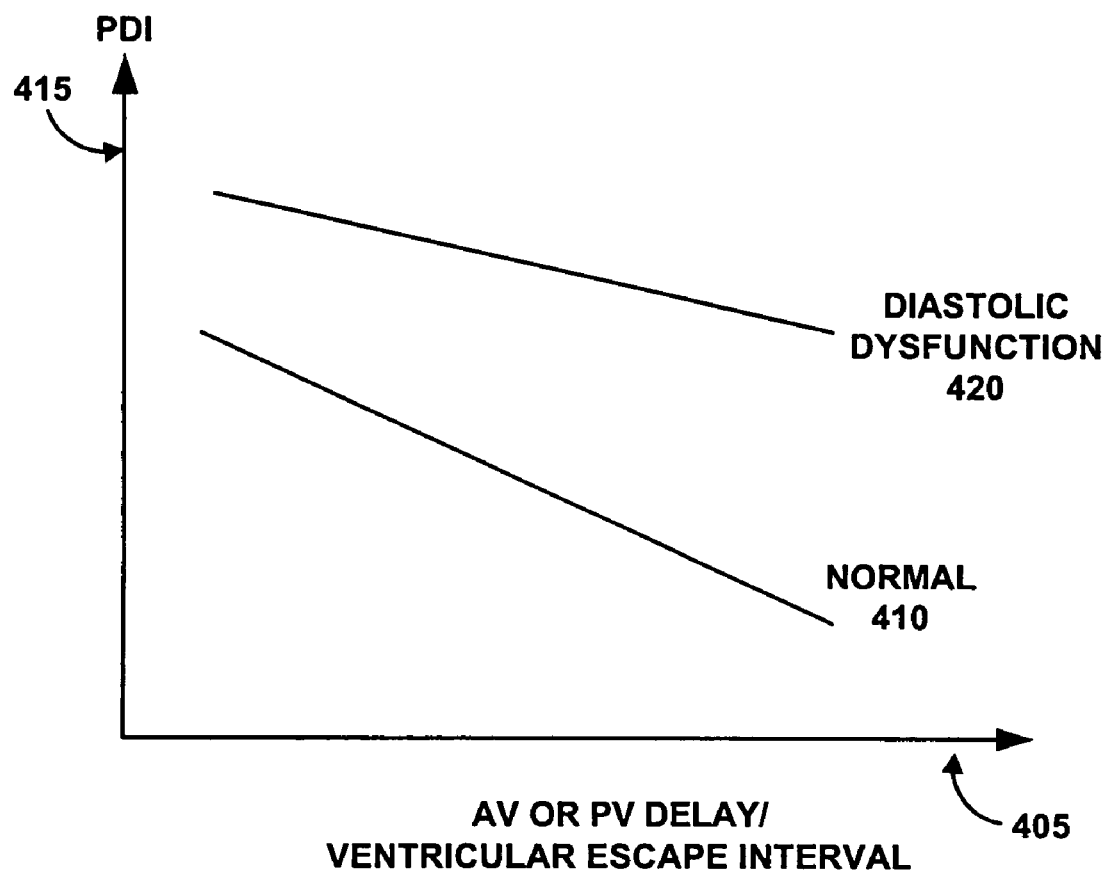
FIG. 4 is a graph depicting the relationship between a paced depolarization integral and an atrial-ventricular delay or a ventricular escape interval during diastolic dysfunction relative to normal diastolic function.

In FIG. 4, a hypothetical slope is sketched representing normal diastolic function 410. This slope is determined by plotting the filling time, as represented by AV or PV delay or escape interval, on the x-axis 405 versus the average paced depolarization integral measured for each setting on the y-axis 415. As the AV or PV delay or escape interval increases, ventricular filling time increases and the paced depolarization integral decreases as shown by the negative slope 410. The decrease in paced depolarization integral with increased filling time reflects the inverse relationship between the paced depolarization integral and end-diastolic volume. When diastolic function becomes compromised, such that diastolic filling declines, the slope of the relationship plotted in FIG. 4 becomes less negative as illustrated by the diastolic dysfunction slope 420. Thus, changes in the slope of the relationship illustrated in FIG. 4 represent changes in diastolic function. Hence, this slope is calculated at step 315 (FIG. 3) as a diastolic function parameter from the collected diastolic function data using a curve-fitting algorithm, for example a least mean squares fit.

At decision step 320, microprocessor 60 determines if a worsening of diastolic function is indicated by the diastolic function parameter. If diastolic function has worsened, adjustments may be made at step 325 in an attempt to optimize the stimulation therapy in a way that would improve diastolic function. In one embodiment, the operating parameters controlling atrial stimulation are adjusted in order to increase the active atrial contribution to ventricular filling. For example, the working margin normally added to the atrial stimulation threshold may be increased to improve the certainty of atrial capture.

At step 330, the diastolic function parameter is stored in memory 94 with corresponding date and time information. Diastolic function data selected to be stored at step 330 may also include the average paced depolarization integrals determined for each delay setting, or each of the paced depolarization integral values determined during a test. Additional data related to the patient or cardiac function may also be stored such as sensed resting or posture state, sensed or stimulated heart rate, or other operating parameters of device 10 in effect at the time of the diastolic function test. The diastolic function data may be downloaded at step 335 to an external device 102 at any time by a physician and displayed in a graphical or tabular format for review and analysis by the physician. The physician may then make treatment decisions based on the diastolic function data collected over time.

Figure 5:
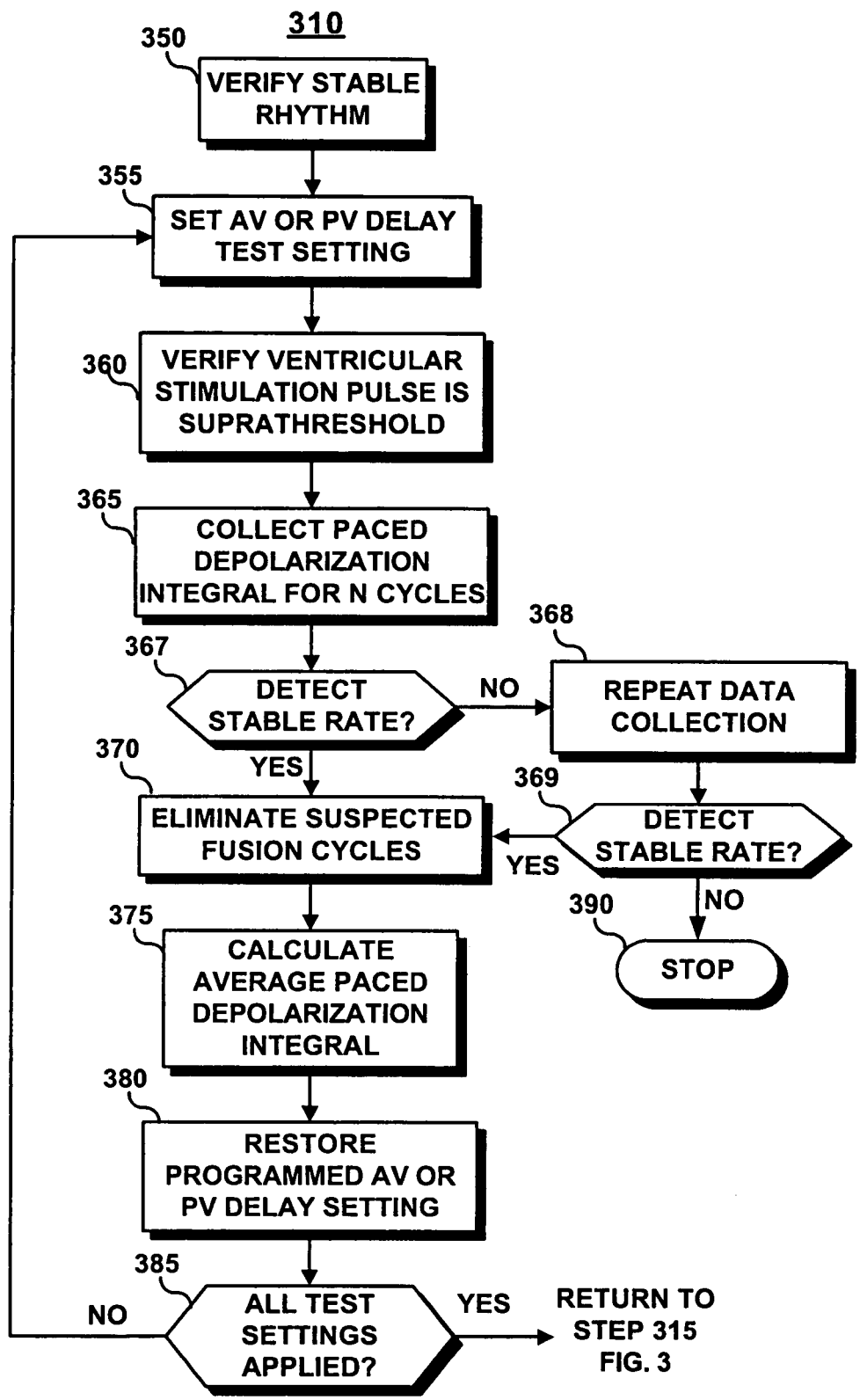
FIG. 5 is a flow chart illustrating a method for collecting diastolic function data, included in the diastolic function test of FIG. 3, during dual chamber or multichamber cardiac stimulation.
Figure 6:
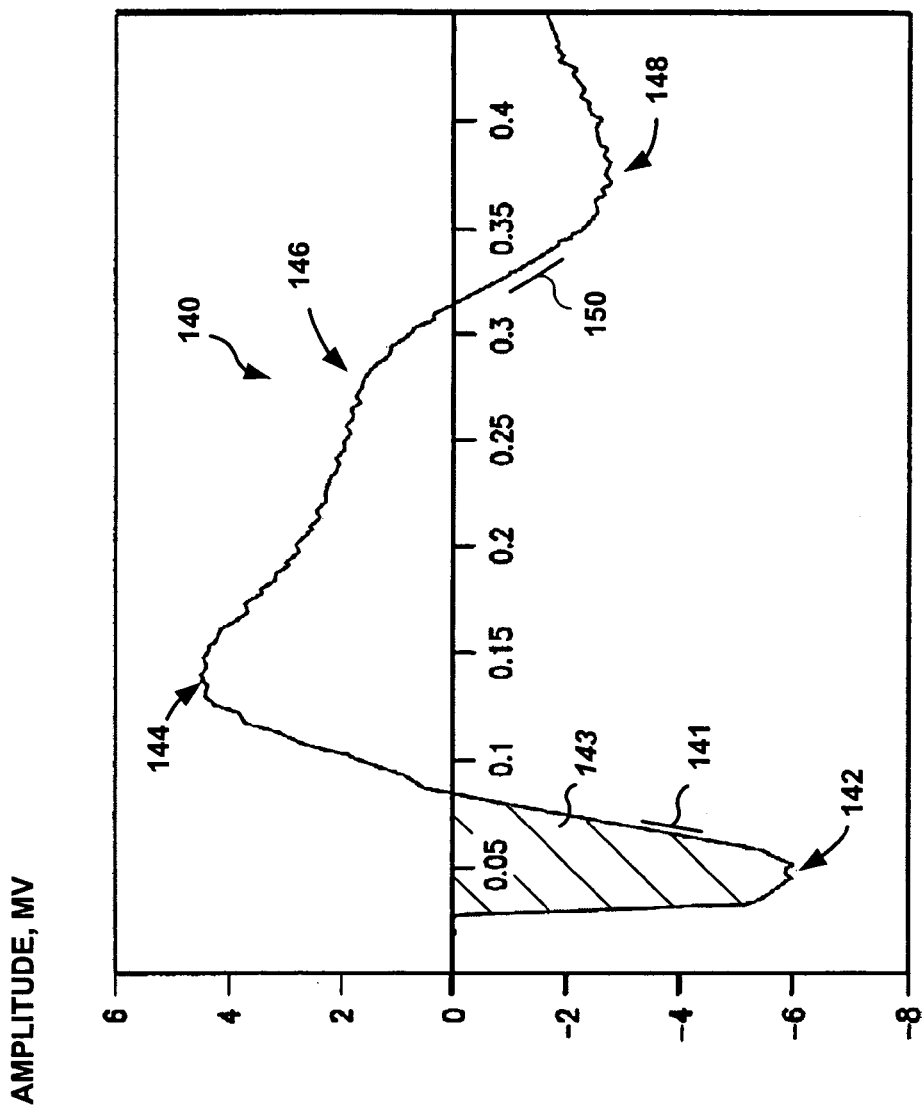
FIG. 6 is a graph depicting an exemplary ventricular evoked response signal that is analyzed to determine the paced depolarization integral during the diastolic function data collection method of FIG. 5.
Figure 7:
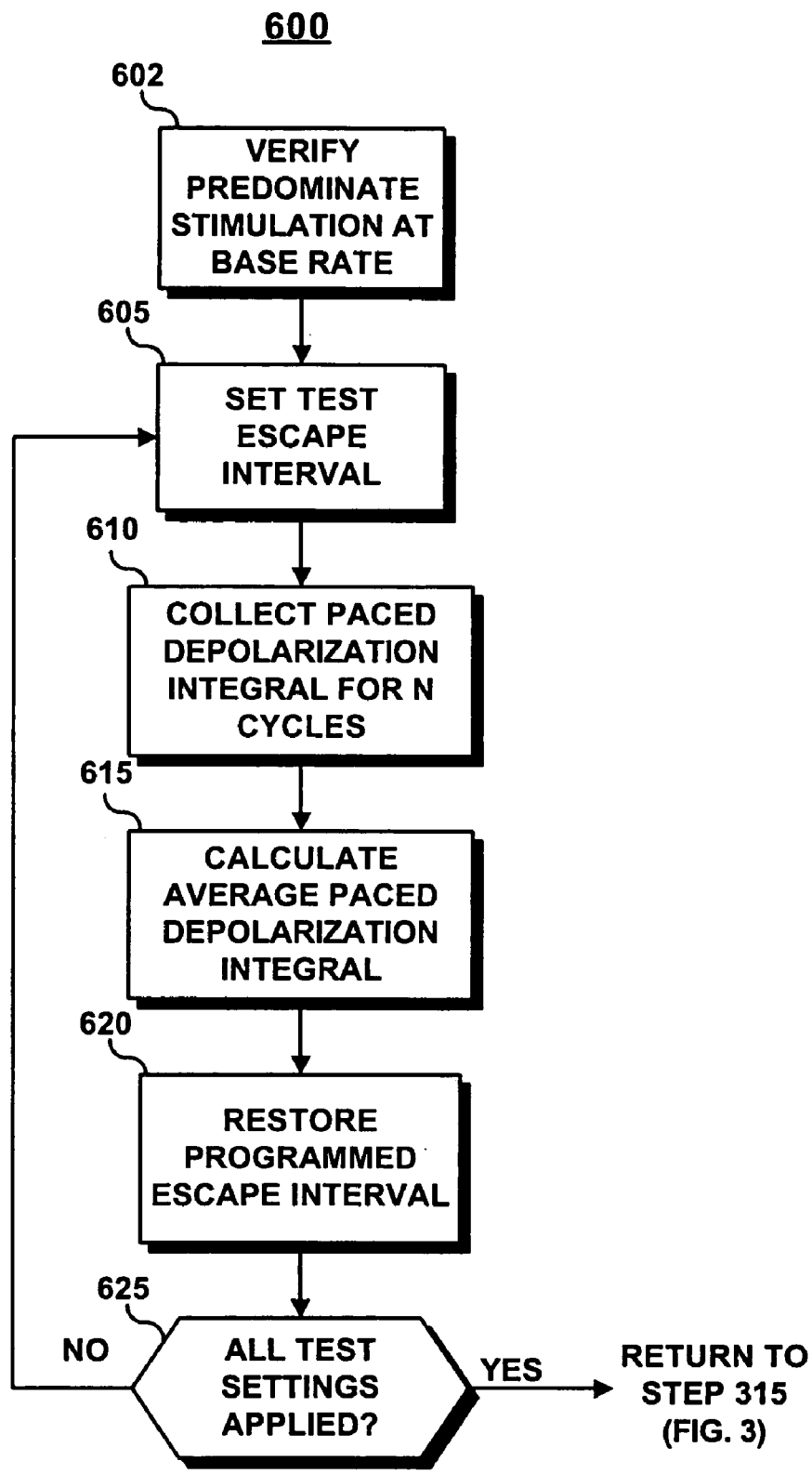
FIG. 7 is a flow chart illustrating a method for collecting diastolic function data, included in the diastolic function test of FIG. 3, during single-chamber ventricular stimulation.

The drawings shown in FIGS. 5 through 7 provide an overview of methods for collecting diastolic function data, as would be performed at step 310 of FIG. 3. The method 310 illustrated in FIG. 5 may be applied in patients having a dual chamber or multi-chamber stimulation device, such as the device 10 shown in FIG. 2. An alternative method for data collection during single chamber ventricular stimulation will be described with reference to FIG. 7 for use in patients having a single chamber stimulation device, or when a dual chamber or multichamber device is operating in a ventricular stimulation only mode.

To ensure reliable data, a stable heart rhythm is preferred during collection of diastolic function data. During dual chamber stimulation, the heart rhythm may be one of atrial stimulation or atrial sensing but in either case should be at a stable rate within a predetermined range of the base stimulation rate in order to prevent interference of diastolic testing functions during periods of rhythm instability. Diastolic data is preferentially acquired during atrial stimulation since the heart rhythm is likely to be more stable than during atrial sensing of the intrinsic heart rhythm. The data collection method 310 shown in FIG. 5 begins by verifying a stable cardiac rhythm at step 350 and determining if the rhythm is predominately sensing or stimulating in the atrium.

If atrial stimulation is predominate, the AV delay is adjusted to one of a number of predetermined AV delay test settings at step 355. If atrial sensing is predominate, the PV delay is adjusted to a predetermined PV delay test setting at step 355. In one embodiment, if the rhythm is fluctuating between atrial sensing and atrial stimulation, or if atrial stimulation is preferred, a stimulation rate slightly above the base rate could be applied to induce atrial stimulation. The test settings may be fixed or may be programmable by a clinician. All test settings applied, however, must be less than the atrioventricular conduction time such that all AV or PV delay settings expire before an intrinsic R-wave occurs. For example, a range of settings from 0 ms to 25 ms less than the interval between an atrial stimulation pulse or sensed atrial P-wave and the next occurring R-wave may be applied. Additionally, a range of shorter AV or PV delay settings, e.g., 0–100 ms, are likely to provide a better diastolic function parameter.

At step 360, the ventricular stimulation pulse output is verified to be set at a level that successfully captures the ventricle. This may be achieved by verifying capture at the prevailing ventricular pulse output setting or by setting the pulse output to a high level guaranteed to capture the ventricle. Preferably, the ventricular pulse output is set well above the capture threshold because the paced depolarization integral value can shift when the stimulation pulse output is nearly equal to the capture threshold. To avoid variations in the evoked response that occurs near the threshold level, a threshold test can first be performed, and the stimulation output is set to a predetermined level, e.g., 1.0 Volts, greater than the threshold.

Next, a predetermined number of paced depolarization integrals are collected at step 360. Device 10 is now programmed such that the ventricular pulse generator 72 delivers suprathreshold ventricular stimulation pulses upon expiration of the test AV or PV delay setting. Following each ventricular stimulation pulse, a paced depolarization integral is obtained. Preferably eight paced depolarization integrals are collected during unipolar sensing of the ventricular signal by A/D converter 90.

Unipolar sensing is preferred because bipolar evoked response signals are less sensitive to changes in ventricular volume. A unipolar sensing configuration is selected by switch 74 by connecting, in the embodiment shown in FIG. 1, either the housing 40 or a coil electrode 28, 36 or 38 as the return electrode in combination with a ventricular tip electrode 32 or 26 or a ventricular ring electrode 34 or 25. For evaluation of right ventricular diastolic function, either right ventricular tip electrode 32 or right ventricular ring electrode 34 may be selected as the sensing electrode.

Depending on the sensitivity of the evoked response signal acquired from the left ventricle to changes in left ventricular volume, monitoring of left ventricular diastolic function may also be possible. For evaluation of left ventricular diastolic function, either left ventricular tip electrode 26 or left ventricular ring electrode 25 may be selected. Other variations that may be possible, depending on the sensitivity of the evoked response signals obtained to changes in ventricular volumes, may include biventricular diastolic function testing or global ventricular diastolic function testing.

In biventricular diastolic function testing, both right and left ventricular diastolic function may be evaluated simultaneously, for example using different inter-ventricular stimulation intervals, or one at time by inhibiting stimulation to one ventricle while collecting paced depolarization integrals in the other ventricle. A paced depolarization integral is determined by sampling the ventricular EGM signal during a detection window set by timing control 79 following the delivery of the ventricular stimulation pulse. All ventricular signal samples occurring during the detection window with a magnitude greater than a predetermined integration baseline are integrated by microprocessor 60 to obtain a paced depolarization integral. The integration baseline can be measured as the zero baseline occurring prior to a stimulation pulse or during the recharge period immediately after the stimulation pulse.

In FIG. 6, a ventricular EGM signal 140 as it might appear following a ventricular stimulation pulse is illustrated. Immediately following a stimulation pulse, is the ventricular evoked response signal 144. All signal samples greater in magnitude, and more relatively negative, than a predetermined baseline during a predetermined detection window, will be integrated to obtain the paced depolarization integral 143. The detection window is set to begin shortly after the ventricular stimulation pulse by timing control circuitry 79 and extend until a zero crossing of the EGM signal 140 occurs or for a predetermined period of time during which an evoked response is expected to occur, typically on the order of 60 ms and no longer than 150 ms.

After collecting a desired number of paced depolarization integrals at the prevailing AV or PV delay test setting a stable rate is again verified at decision step 367. Throughout any given test, the heart rate should remain stable and preferably remain exclusively in an atrial stimulation rhythm or an atrial sensing rhythm, not a mix of both.

If atrial sensing is predominate, such that PV delay test settings are applied, the heart rate preferably remains within a predefined range of the intrinsic rate, for example fluctuations of less than 5 to 10 beats per minute. Or if, atrial stimulation is predominate, such that AV delay test settings are applied, the stimulation rate preferably remains constant throughout the data collection.

If the intrinsic rate or stimulation rate fluctuates by more than a predetermined amount during any given test setting, as determined at decision step 367, any data collected for that setting is discarded, and data collection at that test setting is repeated at step 368. If more than a given number of attempts to collect data are repeated at step 368 with an excessive fluctuation in heart rate still occurring as determined at step 369, the diastolic function test is terminated at step 390 and abandoned until the next scheduled test or the next resting state requirement is met.

If a stable rate is verified at step 367 or 369 such that valid paced depolarization integral data is collected, an average paced depolarization integral is calculated for that test delay setting at step 375 (FIG. 5). Preferably, the device 10 is capable of detecting suspected fusion beats. Fusion occurs when a stimulation pulse is delivered coincidentally with an intrinsic depolarization.

Fusion beats should be eliminated from the paced depolarization integral data since fusion typically distorts the EGM signal and would alter the paced depolarization integral value. Therefore, prior to calculating the average paced depolarization integral at step 375, suspected fusion beats are identified, and paced depolarization integrals collected from fusion beats are eliminated at step 370.

In one embodiment, the average paced depolarization integral determined at step 375 is compared to a predicted value based on a linear fit of other average paced depolarization integrals already determined. If the average paced depolarization deviates from the predicted value by more than a predetermined amount, for example 20%, then this average is presumed to be erroneous due to either loss of capture or fusion beats occurring during the collection of paced depolarization integrals. The diastolic function data collection method 310 is then restarted using a higher ventricular stimulation output or, if near the higher limit of tested AV or PV delays, testing of that AV or PV delay is abandoned.

At step 380, the normally programmed AV or PV delay setting is restored for a predetermined number of cardiac cycles, preferably 30 cardiac cycles. At decision step 385, the microprocessor 60 determines if all designated AV or PV delay test settings have been applied. In order to determine the slope of the relationship illustrated in FIG. 4, a minimum of two points are needed therefore two delay test settings must be applied and the corresponding average paced depolarization integrals determined.

Whenever possible, several test settings are preferably applied in a random order. Each test setting may be applied more than once and is preferably applied three times. If microprocessor 60 determines that additional test settings remain to be applied, the method returns to step 355 to adjust the AV or PV delay to the next test setting. Once all test settings have been applied the desired number of times, as determined at decision step 385, collection of the diastolic function data is complete and the method 310 returns to step 315 of FIG. 3 to calculate the diastolic function parameter.

In an alternative embodiment, rather than integrating the depolarization signal, the peak negative amplitude 142 of the evoked response 140 could also be obtained and averaged in order to determine an average negative peak amplitude for each AV or PV delay test setting. The slope of the average negative peak amplitude versus AV or PV delay is then calculated as the diastolic function parameter. The slope relationship between peak negative amplitude and AV or PV delay will be similar to the relationship shown in FIG. 4. The slope will be negative and become more negative with improving diastolic function and less negative with worsening diastolic function.

In some patients, the peak negative amplitude may provide a better measurement of changes in ventricular volume than the paced depolarization integral and therefore be the preferred parameter to be measured during diastolic function testing. Collection of both peak negative amplitude and paced depolarization integral data may be desired, or a physician may program the diastolic function test to be performed using both parameters, compare the results, then select which parameter should be used for future tests.

The diastolic function test shown in FIG. 3 may also be applied in patients having a single chamber stimulation device or when a dual chamber device is functioning in a ventricular pacing only mode. A method 600 for collecting diastolic function data for these situations is depicted by the flow chart shown in FIG. 7. For these situations, rather than varying an atrial-ventricular delay in order to vary ventricular filling time, the ventricular escape interval may be varied. As the escape interval increases, (as stimulation rate to decreases) ventricular filling time increases.

At step 602, predominate ventricular stimulation is verified. Preferably, ventricular stimulation is occurring at the programmed base rate during 90% or more of the cardiac cycles. Verification of capture may also be performed at this step, or the ventricular stimulation pulse output may be set at a level well above the known ventricular capture threshold. At step 605, the first of a set of test escape intervals is set by timing control 79. The test escape intervals may be fixed or user-programmed. For example, if the base rate is programmed to 75 pulses per minute, test ventricular escape intervals may be set corresponding to the rates of 75, 85, 95 and 105 pulses per minute. At step 610, the paced depolarization integral is obtained for a desired number of cardiac cycles, for example 8 cycles, during ventricular stimulation delivered by ventricular pulse generator 72 upon expiration of the test escape interval. At step 615, the average paced depolarization integral for the prevailing test escape interval is calculated. If the stimulation device is capable of fusion detection, any suspected fusion beats are eliminated from this calculation.

At step 620, the normally programmed escape interval is restored for a desired period of time or number of cardiac cycles, for example 30 cardiac cycles. At step 625, microprocessor 60 determines if all test settings have been applied for a desired number of times, for example three times each. If not, the method returns to step 605 to set the next test escape interval. If data collection is complete, the method returns to step 315 of the diastolic function test (FIG. 3) and calculates the diastolic function parameter based on the collected average paced depolarization data.

Thus, a system and method for performing a diastolic function test has been described. Changes in diastolic function may be used to alter stimulation therapy. Diastolic function data may be stored for later display on an external device and used for diagnostic purposes by a clinician. While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method comprising:
   delivering ventricular stimulation pulses at a plurality of ventricular filling times;
   monitoring evoked responses corresponding to the plurality of ventricular filling times;
   obtaining a diastolic function parameter by processing the evoked responses as a function of the ventricular filling times; and
   determining if there has been a change in diastolic function by comparing the obtained diastolic function parameter to a second diastolic function parameter.

2. The method according to claim 1, further comprising verifying a predetermined state of activity.

3. The method according to claim 1, wherein monitoring evoked responses comprises adjusting AV delays.

4. The method according to claim 1, wherein monitoring evoked responses comprises adjusting PV delays.

5. The method according to claim 1, wherein monitoring evoked responses comprises adjusting cycle lengths.

6. The method according to claim 1, wherein the second diastolic function parameter corresponds to a previously obtained diastolic function parameter.

7. The method according to claim 1, wherein processing the evoked responses comprises determining paced depolarization integrals for the evoked responses.

8. A method comprising:
   delivering ventricular stimulation pulses at a plurality of ventricular filling times;
   monitoring evoked responses corresponding to the plurality of ventricular filling times;
   processing the evoked responses as a function of the ventricular filling times to obtain a diastolic function parameter wherein the obtained diastolic function parameter comprises a slope of a relationship between evoked responses and corresponding ventricular filling times; and
   comparing the obtained diastolic function parameter to a second diastolic function parameter.

9. A method comprising:
   delivering ventricular stimulation pulses at a plurality of ventricular filling times;
   monitoring evoked responses corresponding to the plurality of ventricular filling times;
   processing the evoked responses as a function of the ventricular filling times to obtain a diastolic function parameter; and
   comparing the obtained diastolic function parameter to a second diastolic function parameter, wherein the second diastolic function parameter is indicative of normal diastolic function.

10. A method for determining diastolic function, the method comprising:
    delivering ventricular stimulation pulses at a plurality of ventricular filling times;
    monitoring evoked responses corresponding to the plurality of ventricular filling times;
    processing the evoked responses as a function of the ventricular filling times by calculating a slope of a relationship between evoked responses and atrioventricular delays or cycle lengths; and
    determining diastolic function based on the processing by comparing the slope with a stored value to indicate diastolic function of the heart.

11. A method for determining diastolic function, the method comprising:
    delivering ventricular stimulation pulses at a plurality of ventricular filling times;
    monitoring evoked responses corresponding to the plurality of ventricular filling times;
    processing the evoked responses by determining peak negative depolarization amplitudes as a function of the ventricular filling times; and
    determining diastolic function based on the processing.

12. A cardiac stimulation device comprising:
    at least one electrode that senses cardiac activity;
    a ventricular pulse generator that selectively delivers a ventricular stimulation pulse;

a controller connected to the ventricular pulse generator and the electrode, the controller programmed to control the ventricular pulse generator to deliver ventricular stimulation pulses at various ventricular filling times, to determine at least one feature of each evoked response at the various ventricular filling times, to obtain a diastolic function parameter by processing the evoked responses as a function of the ventricular filling times, and to determine if there has been a change in diastolic function by comparing the obtained diastolic function parameter to another diastolic function parameter.

13. The device according to claim 12, further comprising a physiological sensor that verifies a predetermined state of activity.

14. The device according to claim 12, wherein the controller ensures that a ventricular stimulation pulse will capture the ventricle.

15. The device according to claim 12, wherein the controller adjusts a ventricular stimulation timing parameter for controlling the ventricular filling times.

16. The device according to claim 15, wherein the ventricular stimulation timing parameter comprises any one or more of:
   a first atrial-ventricular delay (AV delay) that follows an atrial stimulation pulse;
   a second atrial-ventricular delay (PV delay) that follows a sensed atrial P-wave; and
   a ventricular escape interval.

17. A cardiac stimulation device comprising:
   means for delivering ventricular stimulation pulses at a plurality of ventricular filling times;
   means for monitoring evoked responses corresponding to the plurality of ventricular filling times;
   means for obtaining a diastolic function parameter by processing the evoked responses as a function of the ventricular filling times; and
   means for determining if there has been a change in diastolic function by comparing the obtained diastolic function parameter to another diastolic function parameter.

18. The device according to claim 17, further comprising means for verifying a predetermined state of activity.

19. The device according to claim 17, wherein the means for monitoring evoked responses comprises means for acquiring paced depolarization integral values.

20. The device according to claim 17, wherein the means for obtaining comprises means for determining a slope of a relationship between the evoked responses and the ventricular filling times.

21. The device according to claim 17, wherein the means for monitoring evoked responses comprises means for adjusting a ventricular stimulation timing parameter for controlling the ventricular filling times.

22. The device according to claim 21, wherein the ventricular stimulation timing parameter comprises any one or more of:
   a first atrial-ventricular delay (AV delay) that follows an atrial stimulation pulse;
   a second atrial-ventricular delay (PV delay) that follows a sensed atrial P-wave; and
   a ventricular escape interval.

* * * * *